United States Patent [19]

Odrich

[11] Patent Number: 5,041,081
[45] Date of Patent: Aug. 20, 1991

[54] OCULAR IMPLANT FOR CONTROLLING GLAUCOMA

[76] Inventor: Ronald B. Odrich, 4710 Livingston Ave., Bronx, N.Y. 10471

[21] Appl. No.: 525,043

[22] Filed: May 18, 1990

[51] Int. Cl.⁵ .............................................. A61M 5/00
[52] U.S. Cl. ............................................. 604/9; 623/4
[58] Field of Search ...................................... 604/8–10, 604/175, 264, 294; 623/4

[56] References Cited

U.S. PATENT DOCUMENTS

| | | | |
|---|---|---|---|
| 3,159,161 | 12/1964 | Ness | 604/8 |
| 3,595,240 | 7/1971 | Mishler | 604/9 |
| 4,037,604 | 7/1977 | Newkirk | 604/9 |
| 4,402,681 | 9/1983 | Haas et al. | 604/9 |
| 4,449,974 | 5/1984 | Messingschlager | 604/175 |
| 4,886,488 | 12/1989 | White | 604/9 |

Primary Examiner—Ronald Frinks
Attorney, Agent, or Firm—Notaro & Michalos

[57] ABSTRACT

The present invention relates in general to ophthalmic implants, and in particular to a new and useful transcleral apparatus for the draining of aqueous humor from the anterior chamber of the eye. The implant comprises a transcleral conduit having an inlet opening at one end thereof for communicating with the anterior chamber of an eye, and an outlet opening at an opposite end of the conduit for draining fluid from the anterior chamber. An elongated subconjunctival channel is connected to the conduit and has an inlet opening at one end of the channel for communicating with the outlet opening of the conduit, the channel having an outlet opening at an opposite end thereof for discharging fluid from the conduit, subconjunctivally over the sclera of the eye. A one-way flow resisting valve is provided in the conduit for allowing a flow of fluid to pass under resistance and in only one direction from the inlet to the outlet of the conduit, whereby pressure in the anterior chamber is relieved while avoiding excessive outflow of fluid from the anterior chamber.

19 Claims, 2 Drawing Sheets

OCULAR IMPLANT FOR CONTROLLING GLAUCOMA

FIELD AND BACKGROUND OF THE INVENTION

The present invention relates in general to ophthalmic implants, and in particular to a new and useful transcleral apparatus for the draining of aqueous humor from the anterior chamber of the eye.

In the past when surgical treatment for glaucoma has been attempted, it has been directed toward creating one or more outflow tracts for the aqueous humor, the liquid which fills the anterior part of the eye. In so doing, intraocular pressure has been reduced and the continued damage to the optic nerve by elevated pressures, has been slowed or halted.

A problem frequently encountered with the creation of an outflow tract is the closing-off or "fibrosis" of the aqueous channel causing a return to the high pressure state in the eye. In an effort to thwart such closing of the drainage tracts, numerous synthetic conduits have been designed and implanted. Without exception these devices are implanted using a conventional surgical approach by creating a flap in the external surface of the eye, allowing access to the intraocular environment "from the outside in". No one device has met with overwhelming success, however. The most frequently encountered problems are:

1. Closing-off of the implanted drain by fibrosis and, thus, a return to a poor outflow state.
2. Excessive outflow leading to a soft, poorly formed eye.
3. Infection which is secondary to the surgical disruption of the eye's anatomic barriers.

A recent advance in this field has been the use of laser technology to create a fistula from within the anterior chamber of the eye. This fistula extends only to the subconjunctival space, leaving the eye's natural barrier—the conjunctiva—entirely intact. This fistulous tract is created using a laser light source delivered at point blank range focussed by a thin fiberoptic tip that is introduced through a small (½ mm.) incision in the peripheral cornea. This procedure is routine and relatively well-tolerated. This technique has come to be known as a "laser sclerotomy ab interno".

Like the older, manually-created filtering procedures, the laser tracts have closed-off with time. It is specifically for maintaining the patency of these filtration sclerotomies, including but not limited to those created by laser, that the apparatus of the present invention has been conceived.

U.S. Pat. No. 3,159,161 to Ness discloses a transcleral implant extending through the trabecular meshwork for controlling glaucoma. The implant has a tubular projection which extends into a surgically drilled hole in the trabecular meshwork and into the anterior chamber of the eye. A curved channel which follows the curvature of the eyeball extends from the projection for draining fluid from the anterior chamber. The implant does not have a conical flange nor an interior valve nor does it have an outlet end with a cage as in the present invention.

The use of a valve for venting fluid from the interior of an eyeball is known per se from U.S. Pat. No. 4,402,681 to Haas et al. The valve structure is installed at a location remote from the anterior chamber, however.

Another approach in treating glaucoma using an implant is disclosed by U.S. Pat. No. 4,428,746 to Mendez. The implant is in the form of a bent synthetic cylindrical member which is surgically positioned under a scleral flap near the trabecular meshwork.

U.S. Pat. No. 4,457,757 to Molteno discloses a tubular implant for draining aqueous humor from the eye to relieve glaucoma. One end of the tube is fitted with a flange for insuring a firm attachment to the eye.

A far more complex implant for relieving glaucoma is disclosed by U.S. Pat. No. 4,521,210 to Wong. The implant lies between the sclera and the choroid or ciliary body of the eye and does not extend through the sclera.

The use of a transcleral tube near the trabecular meshwork of the eye is disclosed by U.S. Pat. No. 4,604,087 to Joseph. The tube is secured by a large band which extends around a major diameter of the eyeball.

A surgically implanted member is taught by U.S. Pat. No. 4,634,418 to Binder, for communicating with the anterior chamber of the eye to drain fluid therefrom by a wicking action.

A method of installation for an intraocular lens using a laser is taught by U.S. Pat. No. 4,738,680 to Herman.

A need remains for an ophthalmic implant which is securely held in the eye in a manner which avoids infection and which avoids the closing-off of the outflow of a aqueous humor, while at the same time avoiding excessive outflow of fluid from the eye.

SUMMARY OF THE INVENTION

An object of the present invention is to provide an ophthalmic implant for controlling glaucoma, comprising: a transcleral conduit having an inlet opening at one end thereof for communicating with the anterior chamber of an eye, and an outlet opening at an opposite end of the conduit for draining fluid from the anterior chamber; an elongated subconjunctival channel connected to the conduit and having an inlet opening at one end of the channel for communicating with the outlet opening of the conduit, the channel having an outlet opening at an opposite end thereof for discharging fluid from the conduit, subconjunctivally over the sclera of the eye; and a one-way flow resisting valve in the conduit for allowing a flow of fluid to pass under resistance and in only one direction from the inlet to the outlet of the conduit, whereby pressure in the anterior chamber is relieved while avoiding excessive outflow of fluid from the anterior chamber.

Another object of the present invention is to construct the transcleral conduit so that it is conical with the larger diameter at its inlet opening then at its outlet opening for firmly seating and sealing the conduit in an opening which is surgically or otherwise formed through the sclera. This both firmly seats the implant for a long-term operation while avoiding infection.

To further mechanically fix the implant to the eye, the conduit carries at its inlet opening an intraocular flange. A subconjunctival flange or wing is also positioned around the outlet opening of the conduit and between the conduit and the channel. The flanges resist axial movement of the conduit in either direction.

A screen or grid may also be provided over the inlet opening of the conduit to filter fluid as it leaves the anterior chamber. A cage is also formed at the outlet opening of the subconjunctival channel to keep the outlet opening open.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
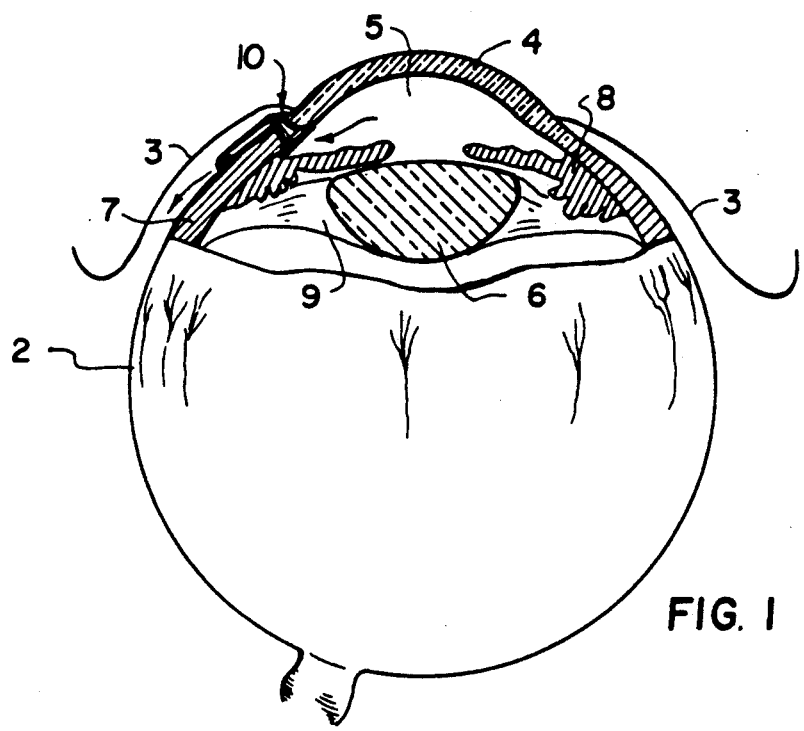
FIG. 1 is a partial sectional view of the eye showing the implant of the present invention in position.

Referring to the drawings in particular, the invention embodied in FIG. 1 comprises an ophthalmic implant generally designated 10 which is constructed so that it is firmly held within an opening which is surgically or otherwise made in the sclera 7 of an eye 2. The surgical incision can be made either mechnically or using a laser. Access is provided into the anterior chamber 5 of the eye, under the cornea 4 for positioning the implant 10 in the sclera 7 and under the conjunctiva 3 of the eye.

In the treatment of glaucoma, increased pressure of fluid within the eye causes a flow of fluid through the muscular support 9 of the lens 6 and around the iris 8 into the anterior chamber 5. To relieve this potentially damaging pressure, the implant 10 of the present invention provides a subconjunctival path for this fluid in a direction of the arrows in FIG. 1.

Figure 2:
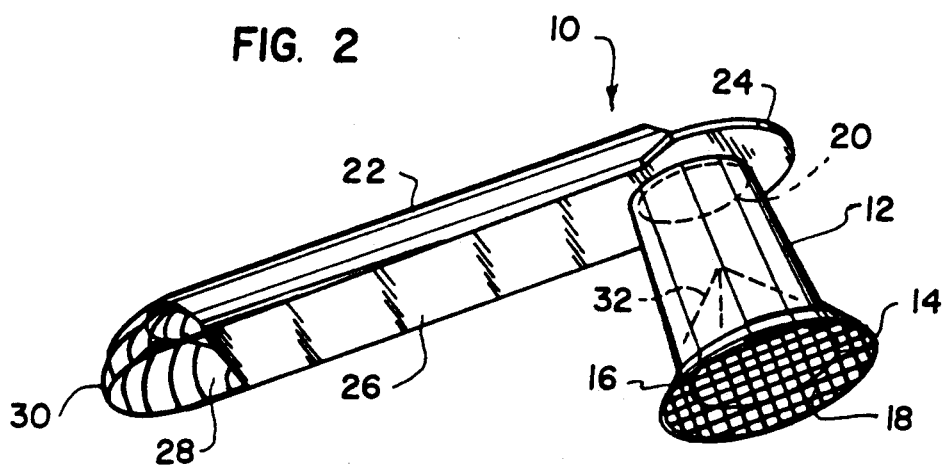
FIG. 2 is a perspective view of the implant on a greatly enlarged scale.

As shown in FIG. 2, implant 10 comprises a conical transcleral conduit 12 which has an inlet opening 14 at one end thereof for communication with the anterior chamber 5. An outlet opening 20 of smaller diameter than the inlet opening 14 is provided at an opposite end of conduit 12. A flange 16 at the inlet end of the conduit 12 carries a screen or grate 18 for filtering the fluid from the anterior chamber and preventing the iris from prolapsing through the implant. Conduit 12 is held axially fixed within the transcleral opening by flange 16, and at its opposite end, by a flange or wing 24 which extends around the outlet opening 20. FIG. 2 also illustrates one embodiment of a one-way flow resisting valve 32 which allows fluid to flow only after it has obtained a certain pressure in the anterior chamber which corresponds to a normal pressure within the anterior chamber, the flow being restricted to only a single direction, out of the anterior chamber 5. In this way, elevated pressure in the anterior chamber 5 which is indicative of glaucoma for example will cause an outward flow of fluid from the anterior chamber through the valve 32. A normal pressure will be maintained within the anterior chamber 5 and the eye 2 as a whole, by the flow resistance of valve 32, to avoid undesirable softening of the eye due to an excessive outflow of fluid which has been experienced with prior implants. Valve 32 may be of any biologically acceptable type, for example in the form of three interacting and resilient flaps which form a valve similar to the tricuspid valve of the heart.

Implant 10 also includes an elongated subconjunctival channel 22 having an inlet corresponding to the outlet 20 of the conduit 12, and an opposite outlet 28 for discharging fluid which has passed along channel 22. A cage 30 surrounds outlet 28 to maintain it in an open condition despite the fact that the channel 22 has been positioned between the outer surface of the sclera and an inner surface of the subconjunctiva. In this way the flow of fluid is kept open for extended periods of time unlike existing implants which have closed after a relatively short operational period.

A flat bottom wall 26 of the channel 22 lies against the outer surface of the sclera for further enhancing the close fit of the implant in the eye.

Figure 3:
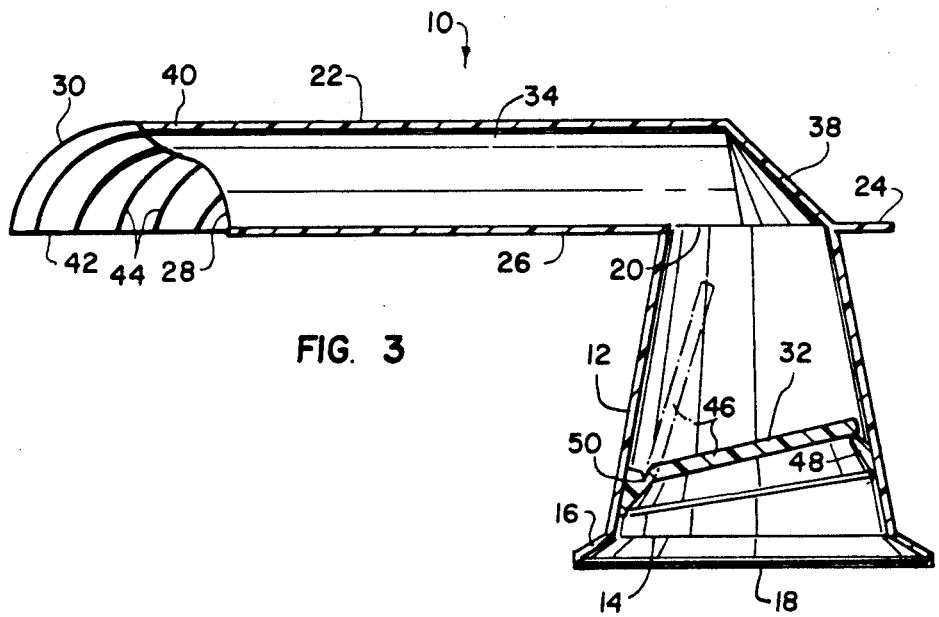
FIG. 3 is a vertical sectional view of the implant on an even larger scale.
Figure 4:
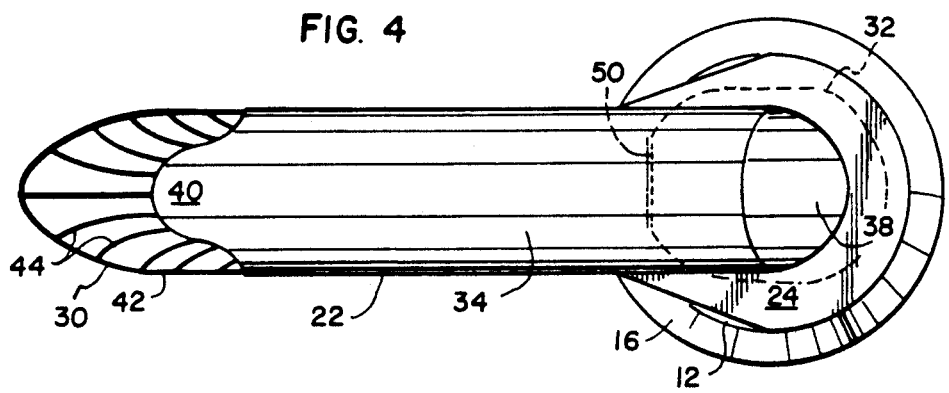
FIG. 4 is a top plan view of the implant.

In FIGS. 3 and 4, where the same reference numeral is utilized to designate the same or similar parts, implant 10 is shown with an alternate embodiment for valve 32. In this case valve 32 comprises a one piece structure which can be fixed, for example by fusing or adhesive onto the inner surface of conical conduit 12. Valve 32 comprises a valve seat member 48 which has a seat facing the outlet opening 20 of the conduit 12. A resilient hinge 50 connects the valve seat 48 to a valve flap 46 which is shown in solid line in its closed position. A phantom line shows the open position for valve flap 46. The resiliency of hinge 50 is selected so that flap 46 does not move to its opened position unless pressure within the anterior chamber has risen to a pathological level. This maintains the normal pressure within the eye while permitting a flow of fluid through the implant when an elevated pressure exists.

Channel 22 includes an upwardly curved portion 34 which forms side and top walls for the channel 22. An inclined rear wall 38 closes the channel around the outlet opening of the conduit 12. The outlet opening 28 of channel 22 includes an overhang 40 which is provided to further help keep the conjunctiva away from the opening 28. The cage 30 is formed by curved rods 44 which curve outwardly and downwardly to meet a lower cage floor rod 42 which forms the shape at the lower end of the cage. Rod 42 is coplanar with the channel floor 26 which in turn is coplanar with the wing or flange 24.

The implant is advantageously made of any bio compatible material such as bio-compatible synthetic plastic as shown, or surgical steel. Valve 32 with its resilient hinge 50 can be made of the same or different material from the rest of the implant, as can the valve 32 of the tricuspid type shown in FIG. 2.

As best shown in FIG. 4, the wing 24 is streamlined with inclined forward surfaces facing the outlet of channel 22. This construction was selected to permit easy entry of the conduit 22 through the opening formed in the sclera, from the anterior chamber, outwardly into the subconjunctivable position shown in FIG. 1. As wing 24 reaches the outer surface of the sclera, flange 16 engages the inner surface of the sclera to firmly hold the implant in place. The structure of wing 24 shown in FIG. 4 permits the implant to be inserted without difficulty, while still axially fixing the conduit 12 in place. The conical configuration for conduit 12 also helps seal the opening through the sclera while also facilitating insertion of the implant.

One preferred embodiment of the invention constructed for an average human adult eye, has an overall length along the channel 22 of approximately 1.675 mm. The height of the channel 22 from its flat scleral wall 26 to the upper end of its upper wall 34 is approximately 0.2 mm. The outlet 20 of conduit 12 has an inside diameter of 0.3 mm while the inlet opening 14 has an inside diameter of 0.5 mm. The outside diameter flange 16 is advantageously 0.65 mm with the length of conduit 12 from its inlet to its outlet openings being approximately 0.6 mm. The width of channel 22 between its side walls is 0.3 mm to form a relatively low, broad and upwardly curved structure which is smoothly and unobtrusively held under the conjunctiva.

While specific embodiments of the invention have been shown and described in detail to illustrate the application of the principles of the invention, it will be understood that the invention may be embodied otherwise without departing from such principles.

What is claimed is:

1. An ophthalmic implant for controlling glaucoma, comprising:
    a transcleral conduit having an inlet opening at one end thereof for communicating with the anterior chamber of an eye, and an outlet opening at an opposite end of the conduit for draining fluid from the anterior chamber, said conduit being conical and said inlet opening of the conduit being larger than said outlet opening of the conduit;
    an elongated subconjunctival channel connected to the conduit and having an inlet opening at one end of the channel for communicating with the outlet opening of the conduit, the channel having an outlet opening at an opposite end thereof for discharging fluid from the conduit, subconjunctivally over the sclera of the eye; and
    a one-way flow resisting valve in the conduit for allowing a flow of fluid to pass under resistance and in only one direction from the inlet to the outlet of the conduit, whereby pressure in the anterior chamber is relieved while avoiding excessive outflow of fluid from the anterior chamber.

2. An implant according to claim 1, including a conical flange connected to the conduit and extending outwardly around the inlet opening of said conduit.

3. An implant according to claim 3, including a wing extending outwardly from the conduit at the outlet opening of the conduit.

4. An implant according to claim 4, wherein said channel has a curved upper wall and a flat lower wall, the flat lower wall being adapted for engagement against an outer surface of the sclera of the eye.

5. An implant according to claim 5, including a cage covering the outlet opening of said channel.

6. An implant according to claim 6, wherein said channel includes an overhang over the outlet opening thereof.

7. An implant according to claim 7, including a screen connected to said conical flange and covering the inlet opening of the conduit.

8. An ophthalmic implant for controlling glaucoma, comprising:
    a transcleral conduit having an inlet opening at one end thereof for communicating with the anterior chamber of an eye, and an outlet opening at an opposite end of the conduit for draining fluid from the anterior chamber;
    an elongated subconjunctival channel connected to the conduit and having an inlet opening at one end of the channel for communicating with the outlet opening of the conduit, the channel having an outlet opening at an opposite end thereof for discharging fluid from the conduit, subconjunctivally over the sclera of the eye;
    a one-way flow resisting valve in the conduit for allowing a flow of fluid to pass under resistance and in only one direction from the inlet to the outlet of the conduit, whereby pressure in the anterior chamber is relieved while avoiding excessive outflow of fluid from the anterior chamber; and
    a cage covering the outlet opening of the channel.

9. An implant according to claim 8, including an overhang connected to the channel and extending over the outlet opening of the channel.

10. An implant according to claim 9, wherein the cage comprises a floor rod which is coplanar to a bottom surface of the channel adapted to lie against an outer surface of the sclera, and a plurality of curved upper rods connected between the channel and the floor rod.

11. An ophthalmic implant for controlling glaucoma, comprising:
    a conical transcleral conduit having an inlet opening at one end thereof for communicating with the anterior chamber of an eye, and an outlet opening at an opposite end of the conduit for draining fluid from the anterior chamber, the inlet opening having a larger diameter than the outlet opening of the conduit; and
    an elongated subconjunctival channel connected to the conduit and having an inlet opening at one end of the channel for communicating with the outlet opening of the conduit, the channel having an outlet opening at an opposite end thereof for discharging fluid from the conduit, subconjunctivally over the sclera of the eye.

12. An implant according to claim 11, wherein the channel has a curved upper wall and a flat lower wall, the flat lower wall being adapted for engagement against the outer surface of the sclera.

13. An implant according to claim 12, including a wing extending outwardly from the channel and around the inlet opening of the channel, the wing being coplanar with the flat bottom wall of the channel.

14. An implant according to claim 13, including a cage covering the outlet opening of the channel.

15. An implant according to claim 11, including a one-way flow resisting valve in the conduit for allowing fluid to flow above a selected pressure and in only one direction from the inlet to the outlet opening of the conduit wherein excess fluid pressure in the eye is relieved while pressure is maintained at a selected normal level of the eye.

16. An implant according to claim 15, wherein the valve comprises a valve seat in at least one resiliently mounted and movable flap for engagement against the valve seat to close the valve and for movement away from the valve seat in a direction from the inlet to the inlet opening of the conduit.

17. An implant according to claim 16, including a conical flange connected to the conduit and extending outwardly around the inlet opening of the conduit.

18. An implant according to claim 17, including a screen connected to the conical flange and extending over the inlet opening of the conduit.

19. An implant according to claim 11, wherein the channel includes an overhang extending over the outlet opening of the channel, and a cage comprising curved rods extending over the outlet opening and a curved bottom rod to which the curved rods are connected to form the cage.

* * * * *